United States Patent
Luciano

(10) Patent No.: US 12,089,926 B2
(45) Date of Patent: *Sep. 17, 2024

(54) FEIGNED INJURY DETECTION SYSTEMS AND METHODS

(71) Applicant: AvaSci LLC, Sparta, NJ (US)

(72) Inventor: Joseph Luciano, Sparta, NJ (US)

(73) Assignee: Joseph Luciano, Sparta, NJ (US)

( * ) Notice: Subject to any disclaimer, the term of this patent is extended or adjusted under 35 U.S.C. 154(b) by 99 days.

This patent is subject to a terminal disclaimer.

(21) Appl. No.: 17/496,473

(22) Filed: Oct. 7, 2021

(65) Prior Publication Data

US 2022/0095959 A1 Mar. 31, 2022

Related U.S. Application Data

(63) Continuation of application No. 16/526,272, filed on Jul. 30, 2019, now Pat. No. 11,166,649.

(60) Provisional application No. 62/712,538, filed on Jul. 31, 2018.

(51) Int. Cl.
| | |
|---|---|
| *A61B 5/11* | (2006.01) |
| *A61B 5/00* | (2006.01) |
| *G06T 7/00* | (2017.01) |
| *G06T 7/246* | (2017.01) |

(52) U.S. Cl.
CPC .......... *A61B 5/1128* (2013.01); *A61B 5/7246* (2013.01); *A61B 5/7282* (2013.01); *G06T 7/0014* (2013.01); *G06T 7/248* (2017.01); *A61B 5/0077* (2013.01); *A61B 2576/00* (2013.01); *G06T 2207/30004* (2013.01); *G06T 2207/30196* (2013.01)

(58) Field of Classification Search
CPC . A61B 2576/00; A61B 5/0077; A61B 5/1114; A61B 5/1121; A61B 5/1122; A61B 5/1128; A61B 5/4528; A61B 5/4571; A61B 5/4576; A61B 5/6804; A61B 5/7246; A61B 5/7282; A61B 5/742; G06T 2207/30004; G06T 2207/30196; G06T 7/0014; G06T 7/246; G06T 7/248
See application file for complete search history.

(56) References Cited

U.S. PATENT DOCUMENTS

| | | | |
|---|---|---|---|
| 5,271,416 A | 12/1993 | Lepley | |
| 5,634,472 A | 6/1997 | Raghuprasad | |
| 8,139,822 B2 | 3/2012 | Selner | |
| 2010/0117837 A1 | 5/2010 | Stirling et al. | |
| 2014/0031668 A1 | 1/2014 | Mobasser et al. | |
| 2014/0243686 A1 | 8/2014 | Kimmel | |
| 2014/0276095 A1 | 9/2014 | Griggs et al. | |
| 2015/0366504 A1* | 12/2015 | Connor ............... | A61B 5/6804 600/301 |
| 2016/0015280 A1 | 1/2016 | Hyde et al. | |
| 2017/0000386 A1 | 1/2017 | Salamatian et al. | |

(Continued)

*Primary Examiner* — Manuchehr Rahmjoo
(74) *Attorney, Agent, or Firm* — Lerner David LLP

(57) ABSTRACT

The present disclosure includes systems and methods for deriving certain characteristics of the patient's body related to motion from captured motion data. The characteristics may be used to compare the characteristics of the supposed injury to the characteristics of a normally functioning body part as well as the functions of an injured body part. The present disclosure provides a reliable and reproducible way to determine whether a supposed injury is a feigned or exaggerated injury or an actual injury.

17 Claims, 16 Drawing Sheets

(56) References Cited

U.S. PATENT DOCUMENTS

2019/0274614 A1    9/2019    Aginsky et al.
2020/0078097 A1*  3/2020    Gregerson ........... A61B 5/1127

* cited by examiner

FEIGNED INJURY DETECTION SYSTEMS AND METHODS

CROSS-REFERENCE TO RELATED APPLICATIONS

This application is a continuation of U.S. application Ser. No. 16/526,272, filed on Jul. 30, 2019, which claims the benefit of the filing date of U.S. Provisional Patent Application No. 62/712,538 filed Jul. 31, 2018, the disclosures of which are hereby incorporated herein by reference.

BACKGROUND OF THE INVENTION

The measurement of physical movements captured by motion capture systems have been used in a multitude of disciplines. For instance, motion capture systems are commonly used by animators, video graphic designers, and game developers to incorporate realistic bodily movements into animations and other computer generated imagery. Motion capture systems have also been used to capture and evaluate physical movements for medical or sports related purposes. However, given the large amount of data collected by motion capture systems, analyzing and otherwise interpreting such data to generate and present data in a coherent and useful manner is critical to maximizing the use of motion capture systems.

BRIEF SUMMARY OF THE INVENTION

Embodiments within the disclosure relate to utilizing motion capture sensors to capture data related to physical movements of a subject or patient's body. The captured data may be analyzed to determine whether the patient's physical movements are consistent with previously collected data representative of a healthy, uninjured movement, an actual injury or a feigned or exaggerated injury. As described herein, the present disclosure provides a reliable and reproducible way to utilize data captured by a motion capture system to determine whether a patient's physical movements are indicative of a feigned or exaggerated injury, an actual injury, or are otherwise indicative of a healthy movement.

A first aspect of the present disclosure includes a method of identifying a category of injury including: receiving coordinates of positions of a first moving body part of a subject using one or more sensors; determining a first set of inflection points of the first moving body part corresponding to the coordinates; comparing the first set of inflection points of the first moving body part to a second set of inflection points of a second moving body part; and identifying a category of injury for the first moving body part according to the comparison with the second moving body part.

In other embodiments, the coordinates may be Cartesian coordinates. The step of comparing may include using a chi-squared test. The category may be one selected from the group consisting of healthy, injured, feigned, and exaggerated. The second moving body part may be a healthy body part. The second moving body part may be a plurality of moving body parts. The plurality of moving body parts may be healthy. The category may be one selected from the group consisting of severely injured, moderately injured, and healthy. The body part may be a shoulder, hip, or leg.

A second aspect of the present disclosure includes a system including a sensor system configured to collect position coordinates of a moving body part, one or more processors. The processor is configured to determine a first set of inflection points of the first moving body part corresponding to the coordinates, compare the first set of inflection points of the first moving body part to a second set of inflection points of a second moving body part, and identify a category of injury for the first moving body part according to the comparison with the second moving body part.

In other embodiments, the category may be one selected from the group consisting of healthy, injured, feigned, and exaggerated. The category may be one selected from the group consisting of severely injured, moderately injured, and healthy. The first and second sets of inflection points may be compared using the chi-squared test.

Another aspect of the present disclosure includes a non-transitory, tangible computer-readable storage medium on which computer readable instructions of a program are stored, the instructions, when executed by one or more computing devices, cause the one or more computing devices to perform a method, the method including: receiving coordinates of positions of a first moving body part of a subject using one or more sensors; determining a first set of inflection points of the first moving body part corresponding to the coordinates; comparing the first set of inflection points of the first moving body part to a second set of inflection points of a second moving body part; and identifying a category of injury for the first moving body part according to the comparison with the second moving body part.

In other embodiments, the category of injury may be one selected from the group consisting of healthy, injured, feigned, and exaggerated. The category of injury may be one selected from the group consisting of severely injured, moderately injured, and healthy.

DETAILED DESCRIPTION OVERVIEW

Aspects of the present disclosure relate to capturing motion data of a patient to determine whether the patient is feigning/exaggerating an injury. For example, sensor systems may collect motion data from a patient which corresponds to a portion of the patient's body which they contend is injured. Such motion data may be collected from the elbow, back, neck, knee, wrist, fingers, and/or other such joints on the patient's body. Characteristic associated with the patient's movements, such as the direction, speed, and/or acceleration of the patient's movements may be determined based on the data captured by the motion capture system. These characteristics may be statistically compared with known characteristics of the patient and/or other patient's movement data which correspond to the same body part. Based upon the comparison and statistical analysis, a determination whether the captured motion data corresponding to the movement of a patient's body part is indicative of a healthy body part, an injured body part, or is indicative of feigned/exaggerated injury.

One such manner in which the motion data may be collected is through the use of sensors, such as optical or reflective sensors, as described in further detail below. After the motion data is collected from the patient, it is analyzed and compared to reference information for each of the categories, which can lead to a determination into which category the patient is in. The reference information for each of the categories displays a unique pattern for the respective category, regardless of certain qualities, such as flexibility or strength, of an individual patient.

Accordingly, the reference information, and the comparisons produce reproducible and reliable results. Moreover, by using a motion capture system, the determination of whether a patient is feigning or exaggerating an injury may be substantially sped up, saving both time and cost.

EXAMPLE SYSTEMS

Figure 1:
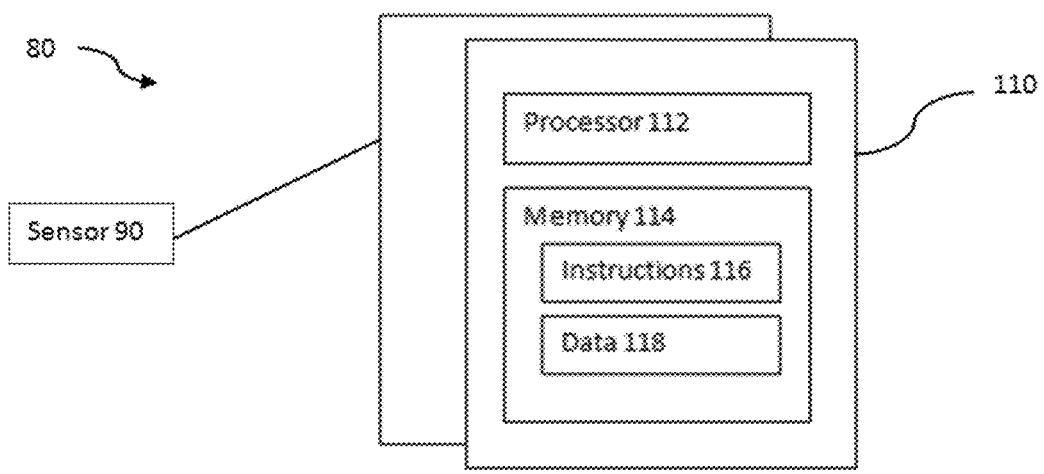
FIG. 1 is a functional diagram of an example system in accordance with aspects of the present disclosure.

FIG. 1 illustrates an example system 80 in which the features described above may be implemented. It should not be considered as limiting the scope of the disclosure or usefulness of the features described herein.

In this example, system 80 can include one or more computing devices 110 and one or more sensor systems 90. Sensor system 90 may include one or more sensors which collect three-dimensional motion data from the patient and transmit the data to the computing device 110. Sensor system 90 track the movement of at least one joint and/or allow for full body capture. The sensors of the sensor system 90 can collect Cartesian coordinate data indicative of position of the optical markers on the body part during motion relative to a reference point. Such reference point (or points) may be positioned on the patient or relative to the patient, such as a stationary sensor in the vicinity of the patient. Alternatively or in combination, the sensors may collect images that may be used to determine the relevant characteristics, described in further detail below. The data can be transmitted to computing device 110. The sensors may transmit the data wirelessly to computing device 110. In some instances, the sensors may include a gyroscopic sensor and/or an accelerometer.

In some embodiments, the sensor system 90 may be an optical motion capture system. The optical motion capture system may be passive or active. The passive optical motion capture system may include passive optical markers, such as a reflective surface which reflects a light, such as an IR light. In some instances, the optical markers may be active, such that they have their own light sources. For instance, the active optical marker may include a pulsed-LED, continuous-LED, or other infrared light emitting devices. In the event a pulsed-LED is used it can be configured such that it pulses at a rate of 1000 Hz or more or less.

The sensor system may include a camera or other such device configured such that it is synchronized or otherwise capable of capturing the reflected or pulsed light. Based upon the captured reflected or pulsed light, the sensor system may determine the position of the optical markers. For instance, the camera may be configured to capture image data corresponding to the optical markers at a rate of about 50-400 frames per second (FPS), or more or less. In some examples, the camera may collect at a rate of about 100 frames per second. Based upon the captured image data, the location of the optical marks to within 1 mm, or more or less, may be determined by the sensor system 90 or computing device 110.

The optical markers may be incorporated onto a body suit which the patient wears. For instance, the suit may be a full body suit. Alternatively, partials body suits, such as arm bands, knee bands, neck bands, etc. may be used.

Computing device 110 can contain one or more processors 112, memory 114 and other components typically present in general purpose computing devices. Memory 114 of computing device 110 can store information accessible by the one or more processors 112, including instructions 116 that can be executed by the one or more processors 112.

Memory 114 can also include data 118 that can be retrieved, manipulated or stored by the processor 112. The memory can be of any non-transitory type capable of storing information accessible by the processor, such as a hard-drive, memory card, ROM, RAM, DVD, CD-ROM, write-capable, and read-only memories.

The instructions 116 can be any set of instructions to be executed directly, such as machine code, or indirectly, such as scripts, by the one or more processors. In that regard, the terms "instructions," "application," "steps" and "programs" can be used interchangeably herein. The instructions can be stored in object code format for direct processing by a processor, or in any other computing device language including scripts or collections of independent source code modules that are interpreted on demand or compiled in advance.

Data 118 can be retrieved, stored or modified by the one or more processors 112 in accordance with the instructions 116. For instance, although the subject matter described herein is not limited by any particular data structure, the data can be stored in computer registers, in a relational database as a table having many different fields and records, or XML documents. The data can also be formatted in any computing device-readable format such as, but not limited to, binary values, ASCII or Unicode. Moreover, the data can comprise any structure and/or format sufficient to identify relevant information, such as numbers, descriptive text, proprietary codes, pointers, references to data stored in other memories such as at other network locations, or information that is used by a function to calculate other data. Data may include data captured by the one or more sensor systems 90.

The one or more processors 112 can be any conventional processors, such as a commercially available CPU. Alternatively, the processors can be dedicated components such as an application specific integrated circuit ("ASIC") or other hardware-based processor. Although not necessary, one or more of computing devices 110 may include specialized hardware components to perform specific computing processes, such as decoding video, matching video frames with images, distorting videos, encoding distorted videos, etc. faster or more efficiently.

Although FIG. 1 functionally illustrates the processor, memory, and other elements of computing device 110 as being within the same block, these components may comprise multiple processors, computers, computing devices, or memories that may or may not be stored within the same physical housing. For example, the memory can be a hard drive or other storage media located in housings different from that of the computing devices 110. Accordingly, references to a processor, computer, computing device, or memory will be understood to include references to a collection of processors, computers, computing devices, or memories that may or may not operate in parallel.

The system 80 may include a storage system 150 capable of storing information accessible by the computing device 110, such as a hard-drive, a solid state hard drive, NAND memory, ROM, RAM, DVD, CD-ROM, write-capable, and read-only memories. In addition, storage device may include a distributed storage device where data is stored on a plurality of different storage devices which may be physically located at the same or different geographic locations, such as network attached storage. The storage device may be connected to the computing devices via a network (not illustrated).

EXAMPLE METHODS

Figure 2:
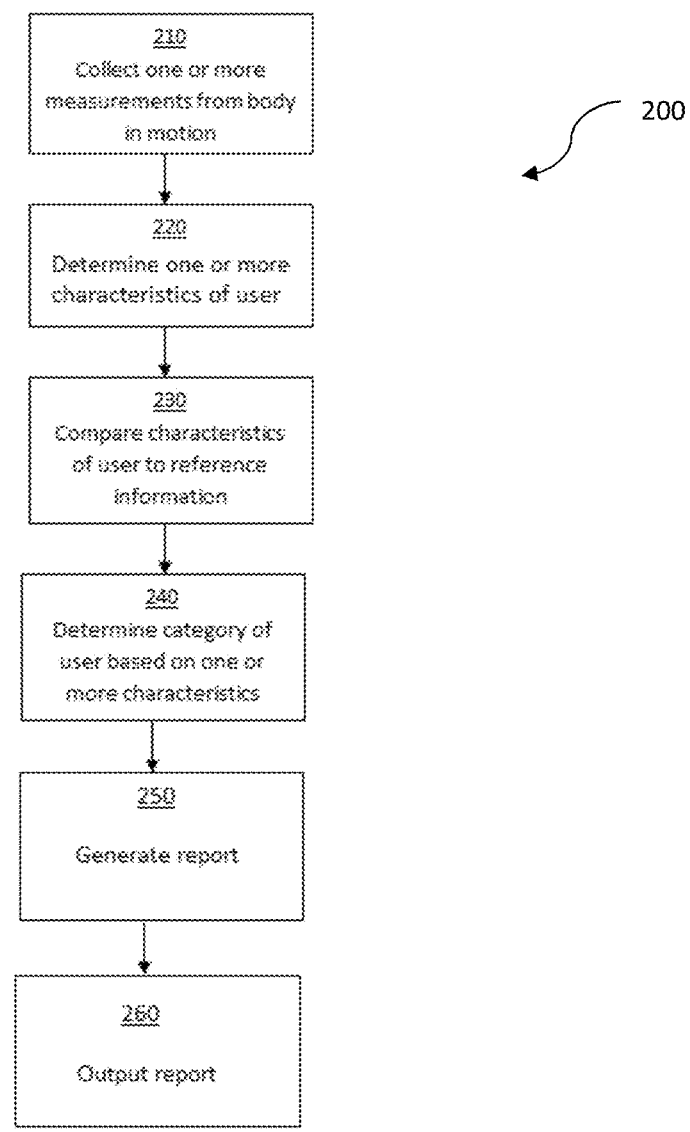
FIG. 2 is an example flow diagram in accordance with aspects of the present disclosure.

FIG. 2 shows an example flow diagram 200 in accordance with aspects of the present disclosure. The operations involved in the methods need not be performed in the exact order described. Rather, various operations may be handled in different order or simultaneously, and operations may be added or omitted.

At block 210, motion data may be collected from a patient at a single joint, such as a shoulder, at multiple joints, or data may be collected from the full body of the patient. In this regard, the data may be collected while the joint(s) and/or body is in motion and equipped with a motion capture device. For instance, the motion data may be collected by sensors of the sensor system 90, as described above, or in any other way known in the art.

The sensors may collect data representative of the position, orientation, velocity, and/or acceleration of the joint(s) and/or body being measured. Alternatively, or in addition to, the sensors may collect images that can be used to determine certain characteristics, such as inflection points, angular speed, etc., described below. For instance, the sensor system 90 may capture images of the sensors and transmit such data to the computing device, such as computing device 110 of system 80. Using visual motion algorithms, the computing device 110 may track the motion of the sensors from frame to frame to determine the position of the joint being measured. The position data may be in the form of Cartesian coordinates, or other such coordinate system. Although collection of a patient's single joint is described, the motion data may correspond to the movement of multiple joints. For instance, the motion data may correspond to the movement of a wrist in conjunction with an elbow.

At block 220, all or a portion of the data is received by the processor and analyzed using instructions, such as instructions 116, to determine one or more characteristics related to the patient's motion. For example, FIGS. 3-10 show characteristics based on the movement of a patient's right shoulder. Such characteristics include, as shown in FIGS. 3-10, angular speed, inflection points, abduction (ABD), angle speed, right angle distribution, and speed distribution. The characteristics listed above and described in further detail below, are not intended to limit the scope of the disclosure to such characteristics, rather, it is intended that any characteristic related to the motion of a joint of the body may be considered at block 220.

At block 230, one or more of the patient's characteristics are compared to one or more corresponding characteristics of the reference information, which is a database of a collection of these same characteristics from a plurality of subjects, such that the database includes the characteristics, e.g. angular speed, inflection points, angle speed, right angle distribution and speed distribution. The reference information of the database includes information for a healthy body part or joint of a plurality of subjects. Alternatively or in addition, the database can include reference information for each of the categories, including healthy, injured, feigned and exaggerated injuries. At least one of the patient's characteristics is compared to the reference information for at least one of the following: a healthy shoulder, an injured shoulder, a feigned injury of a shoulder, and an exaggerated injury of a shoulder. The patient's characteristics may be compared to each of the four categories, or it may be compared to any combination of the categories, or a single category. For example, in one instance, the patient's characteristics may be compared to reference information corresponding to healthy shoulders of a plurality of individuals.

As described in greater detail herein, certain of the characteristics are determined to produce distribution data, such as distribution data of the inflection points of the patient's movement. The patient's distributions are statistically analyzed and compared to distribution data corresponding to the collected reference information for that healthy body part. The statistical significance of the comparison shows the relative consistency of the movement of the patient. Healthy subjects present inflection points of consistent patterns, whereas, feigned and exaggerated movements are inconsistent when the movement is repeated.

The comparison is determined with a statistical analysis of the distribution of inflection points for the subject's movement compared with the distribution of inflection points for the reference information of at least one of the categories (healthy, injured, feigned, and exaggerated). In one example, the distribution data of the inflection points of healthy reference information is set as the null hypothesis and the statistical difference between the null hypothesis and the subject's distribution data of inflection points is determined, such as by the 2D Histogram Hypothesis Test or the chi-squared test. The comparison determines the probability that the null hypothesis is true.

Additionally or alternatively, the K-means analysis may be used to identify clusters of observations of the inflection points in the data sets for the subject's movement. The Analysis of Variance test (ANOVA) test may be applied to determine the statistical significance of the subject's movement and the movements of healthy subjects.

At block 240, the category into which the patient falls is identified based on the statistical analysis performed at block 230. For example, in block 230, the statistical probability of the null hypothesis being true determines the category into which the subject falls. For example, if the chi-squared test is used in the statistical analysis and produces a result of the p-value being less than or equal to the significance level of 0.05 (p-value=0.05) with a level of confidence of about 95%, the null hypothesis is rejected such that there is a statistically significant difference in the subject's inflection points and that of the healthy movement reference information. At this point, it is determined whether the patient has a healthy body part, injured body part, or is feigning or exaggerating an injury.

At block 250, a report is generated. The report may show the category into which the patient falls. Alternatively or in combination, the report may show the characteristics for the patient and/or the reference information. The report showing the characteristics of the patient and reference information may be in graph form. At block 260, the report is outputted for receipt and use by an operator. An operator, such as a trained physician, may confirm the results of the outputted report.

In an alternative embodiment, rather than being performed by the computing device, blocks 230 and 240 may be performed by an operator. In this embodiment, block 250 generates a report displaying the determined characteristics for the patient and the corresponding characteristics for at least one of the categories (healthy, injured, and/or feigned/exaggerated injury) of the reference information.

FIGS. 3-10 show a variety of generated reports for healthy, injury, feigned and exaggerated injuries that are each unique to the category (healthy, injured, feigned, exaggerated), such that each report does not depend on specific qualities of a patient, such as flexibility, strength, etc. In particular, each of FIGS. 3-10 includes graphical results of reports of the characteristics related to the motion of right shoulders. Within each set of the figures, those denoted "A" correspond to a healthy shoulder, each of the figures denoted "B" correspond to an injured shoulder, each of the figures denoted "C" correspond to a shoulder feigning an injury, and each of the figures denoted "D" correspond to a shoulder exaggerating an injury. Generally speaking, as discussed in further detail herein, the healthy and injured body parts produce more consistent movements than those body parts having feigned and exaggerated injuries.

Figure 3A:
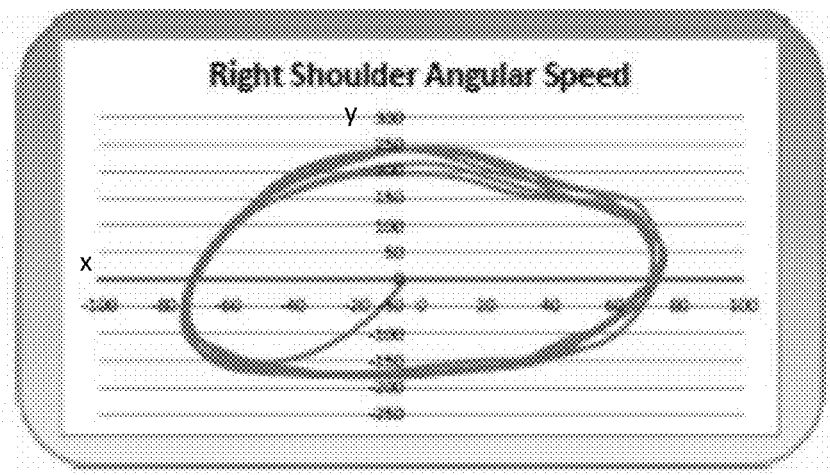
FIGS. 3A, 3B, 3C, and 3D show graphs of results of the angular speed of a right shoulder for a healthy, injured, feigned injury, and an exaggerated injury, respectively.
Figure 3B:
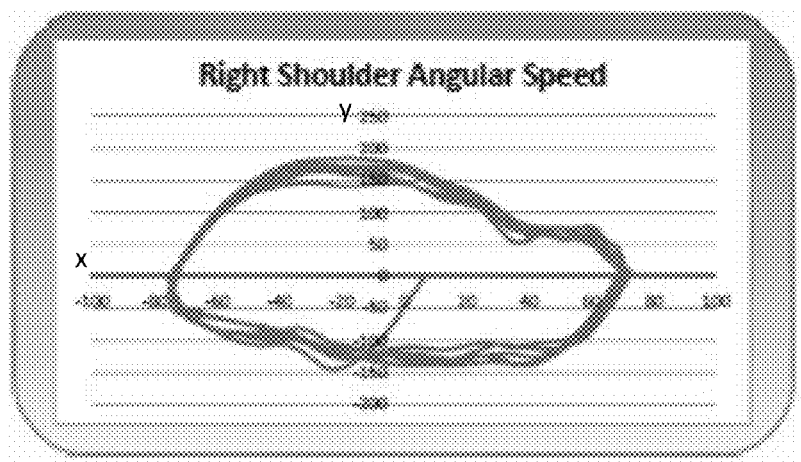
Figure 3C:
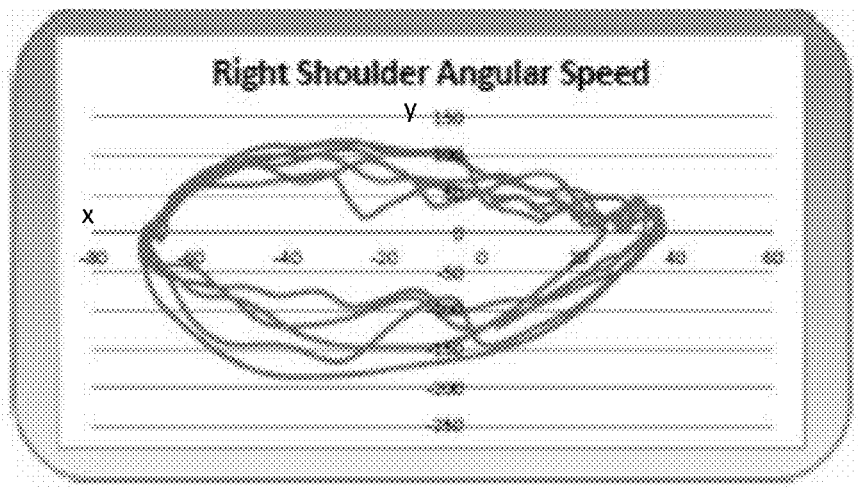
Figure 3D:
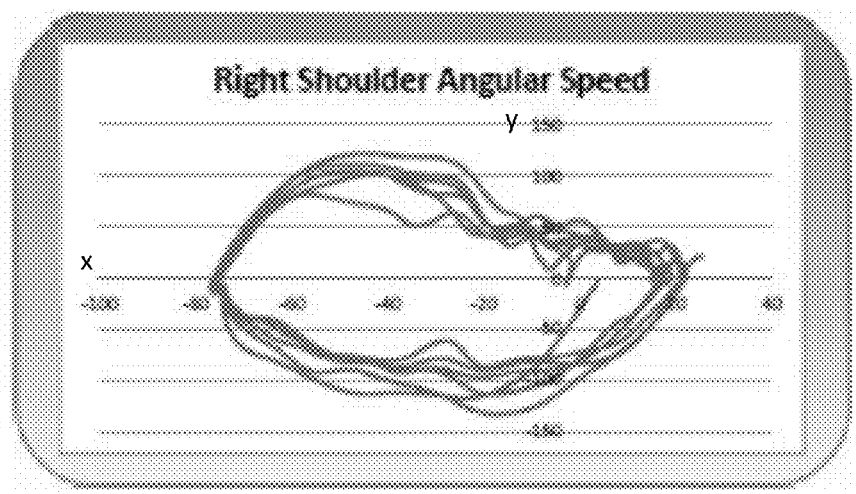

FIGS. 3A, 3B, 3C, and 3D show generated reports for the angular speed of right shoulders. In the graphs, the x-axis represents the angle over time that the movement is performed and the y-axis represents the angular speed over time that the movement is performed. As shown in FIGS. 3A, 3B, 3C, and 3D, each category demonstrates a unique rotational position and angular speed pattern. For example, the healthy shoulder in FIG. 3A demonstrates a consistently repeated rotational position pattern, having consistent correlation between the rotational position and the angular speed of the shoulder. Additionally, an injured shoulder will show points of inflection in the same area with each repetition. As shown in FIGS. 3C and 3D, the feigned and the exaggerated injuries exhibit more inconsistent, less repeated patterns of rotational position and angular speed of the shoulder. Further, the reports corresponding to the feigned and exaggerated injuries do not include one defined point of interest as in the injured shoulder.

FIGS. 4A, 4B, 4C, and 4D illustrate a pattern of inflection points of right shoulders based on the angular speed and rotational position of FIGS. 3A-3D. The graphs of FIGS. 4A-4D include marked points that represent each point that has a value higher or lower than at least two of the previously captured points. In other words, the inflection points represent local maximum and minimums of the angular speed and the rotational position of the shoulder. In some examples, the inflection points may be required to exceed a certain threshold to include only the points of significance. The lighter grey, triangular marked points 410 indicate the inflection points based on rotational position, and the darker grey, circular marked points 414 indicate the inflection points based on angular speed. For ease of illustration, only a single inflection point for each of the rotational position and the angular speed is marked.

Figure 4A:
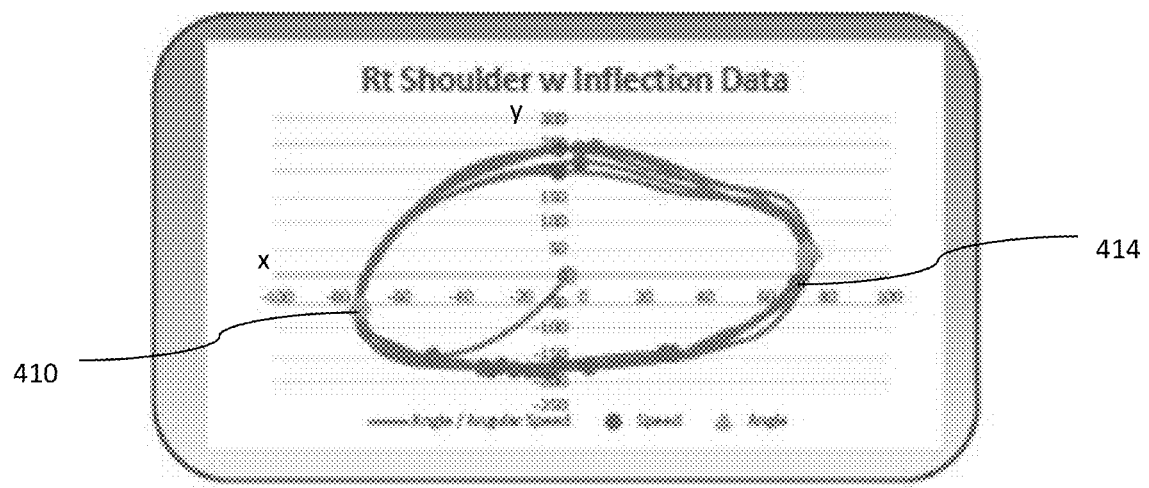
FIGS. 4A, 4B, 4C, and 4D show graphs of results of the inflection points of a right shoulder for a healthy, injured, feigned injury, and an exaggerated injury, respectively.
Figure 4B:
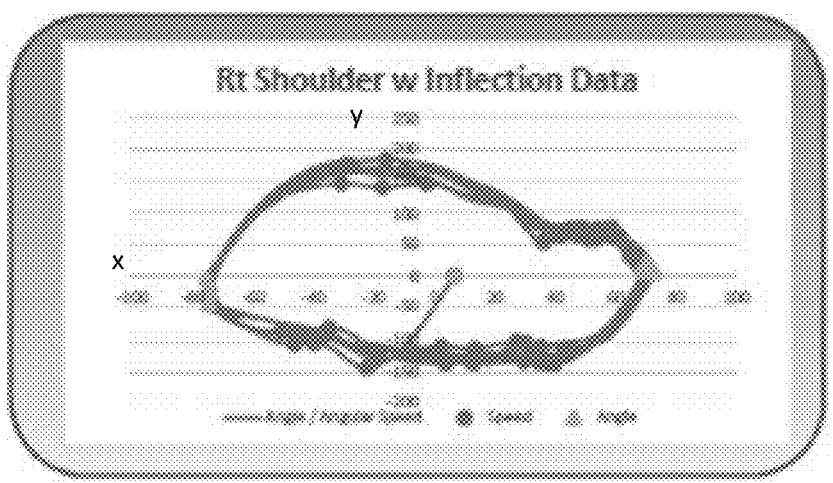
Figure 4C:
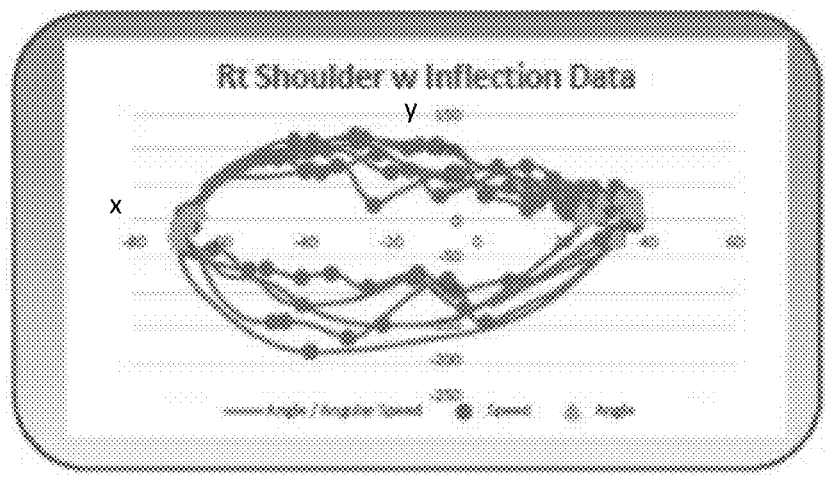
Figure 4D:
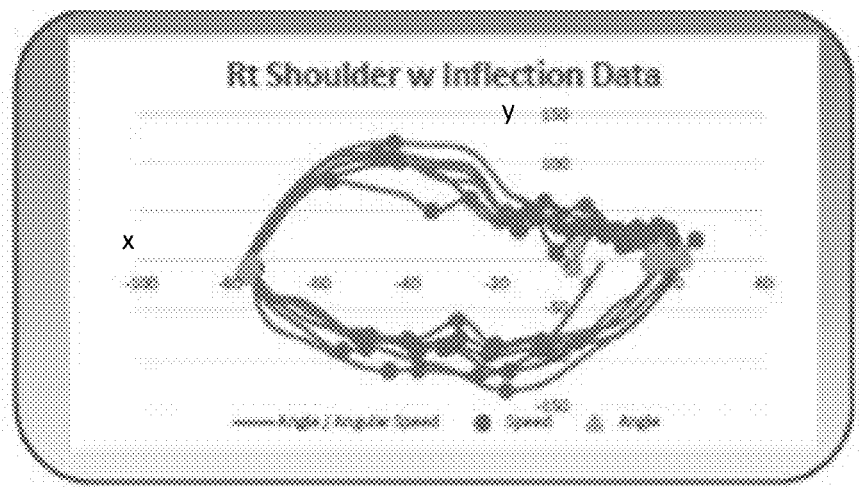
Figure 5A:
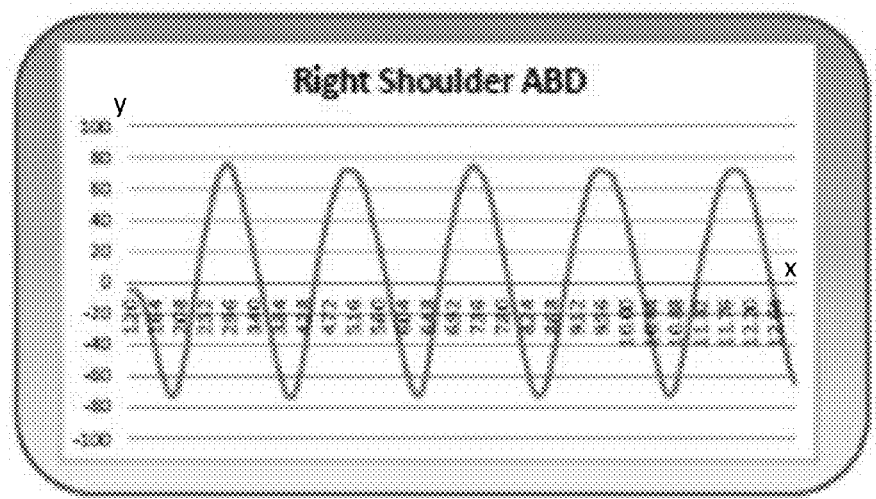
FIGS. 5A, 5B, 5C, and 5D show graphs of results of the abduction (ABD) of a right shoulder for a healthy, injured, feigned injury, and an exaggerated injury, respectively.
Figure 5B:
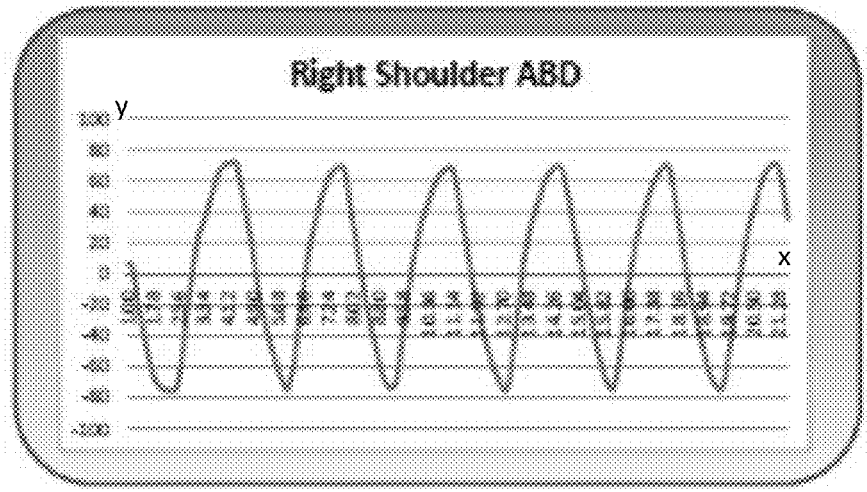
Figure 5C:
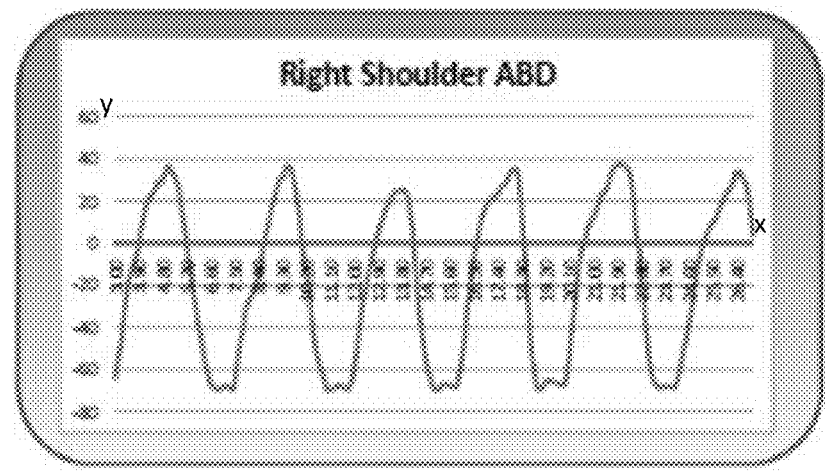
Figure 5D:
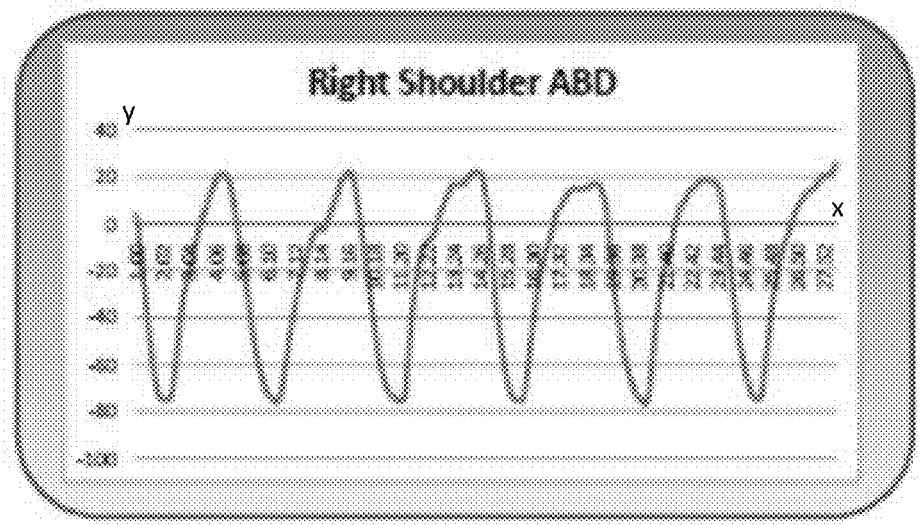
Figure 6A:
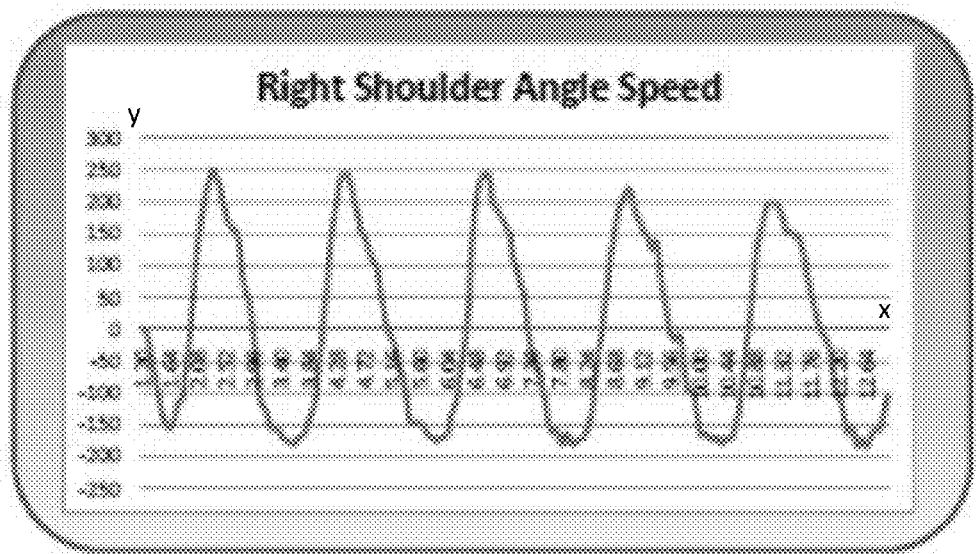
FIGS. 6A, 6B, 6C, and 6D show graphs of results of the angle speed of a right shoulder for a healthy, injured, feigned injury, and an exaggerated injury, respectively.
Figure 6B:
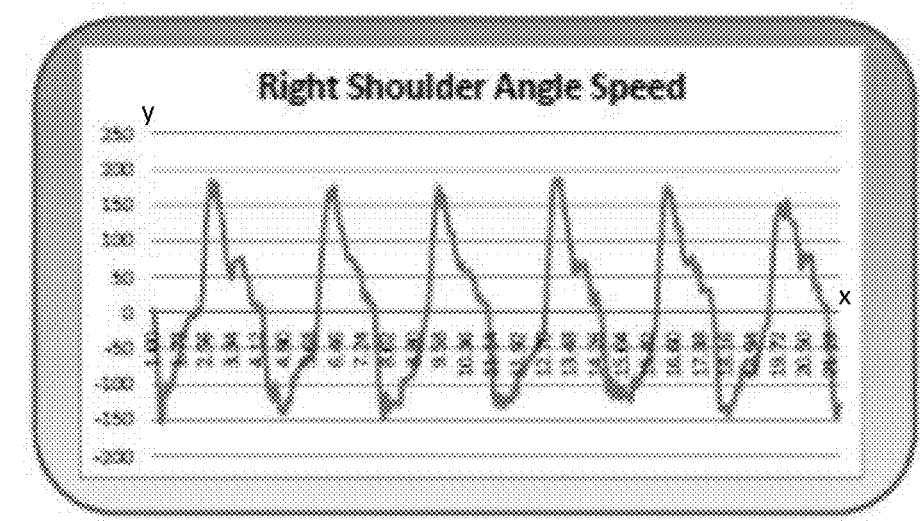
Figure 6C:
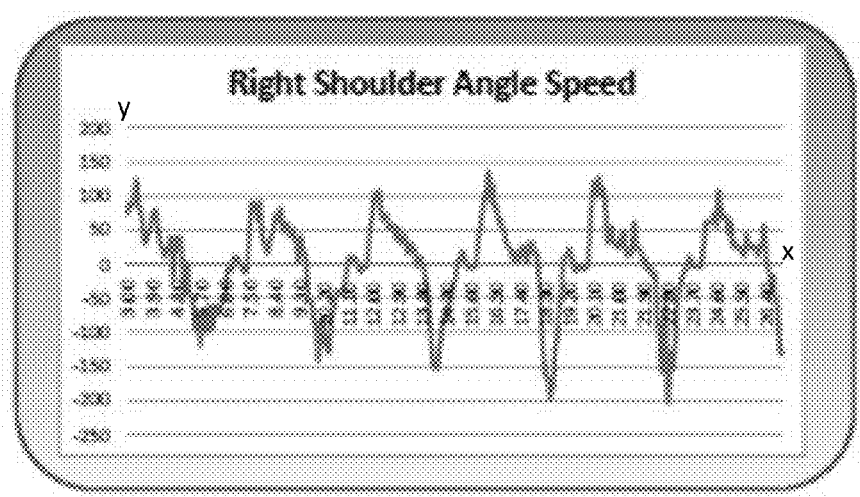
Figure 6D:
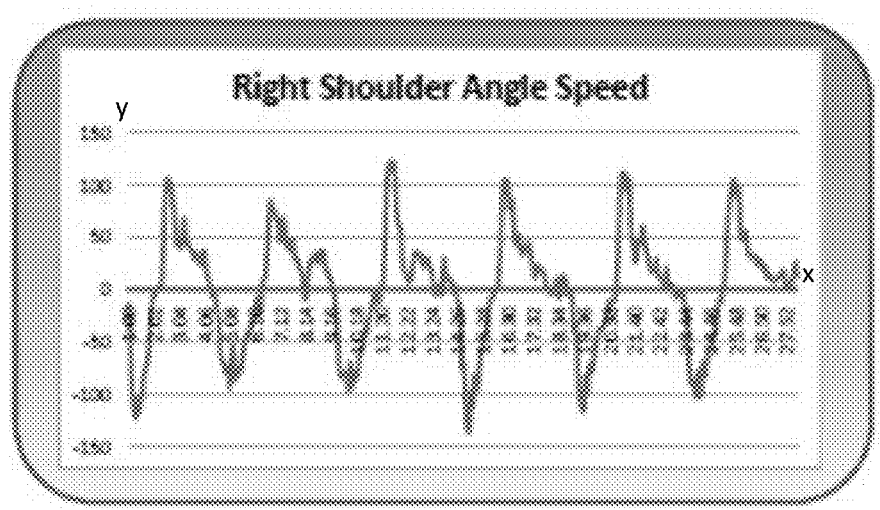
Figure 7A:
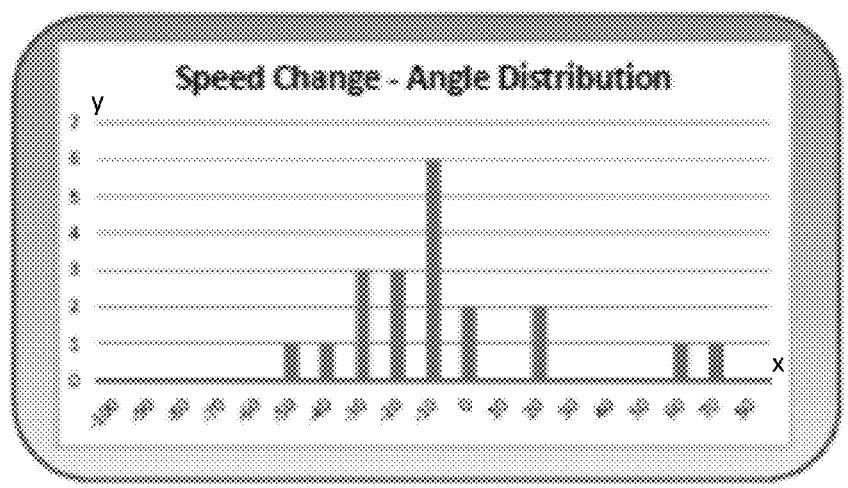
FIGS. 7A, 7B, 7C, and 7D show histogram graphs of results of the speed change, angle distribution of a right shoulder for a healthy, injured, feigned injury, and an exaggerated injury, respectively.
Figure 7B:
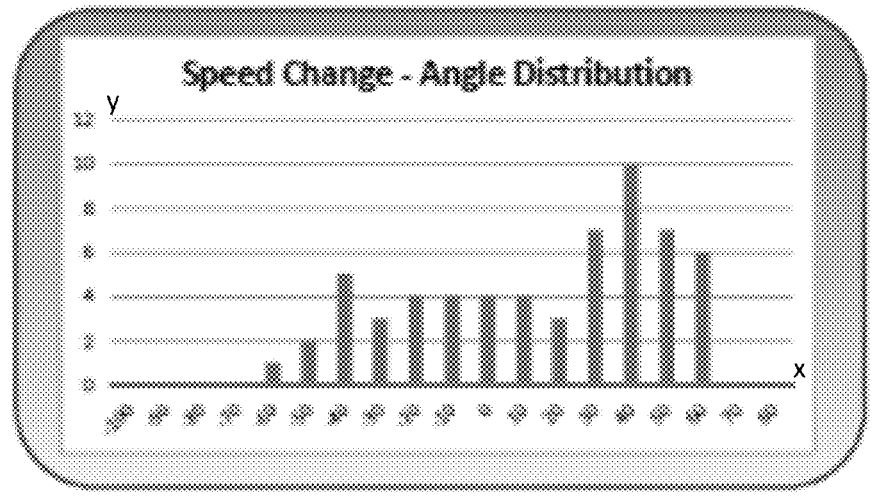
Figures 7C, 7D:
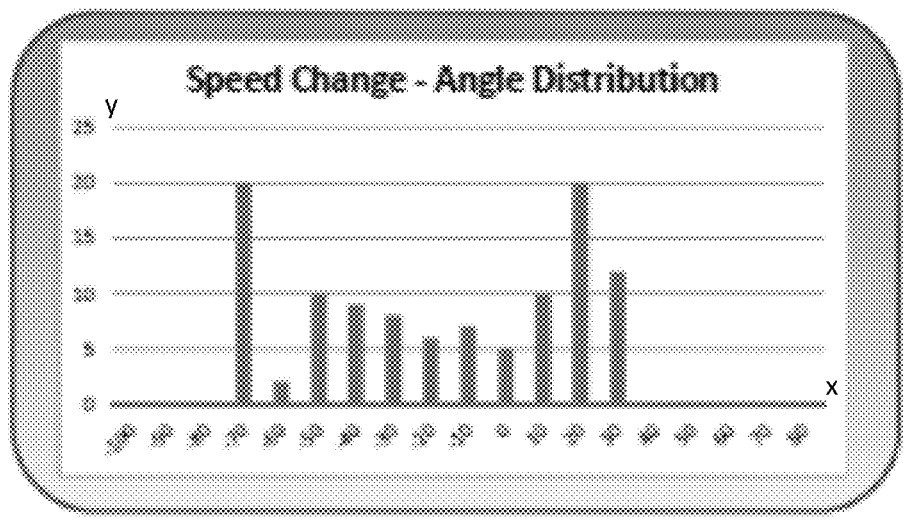
Figure 8A:
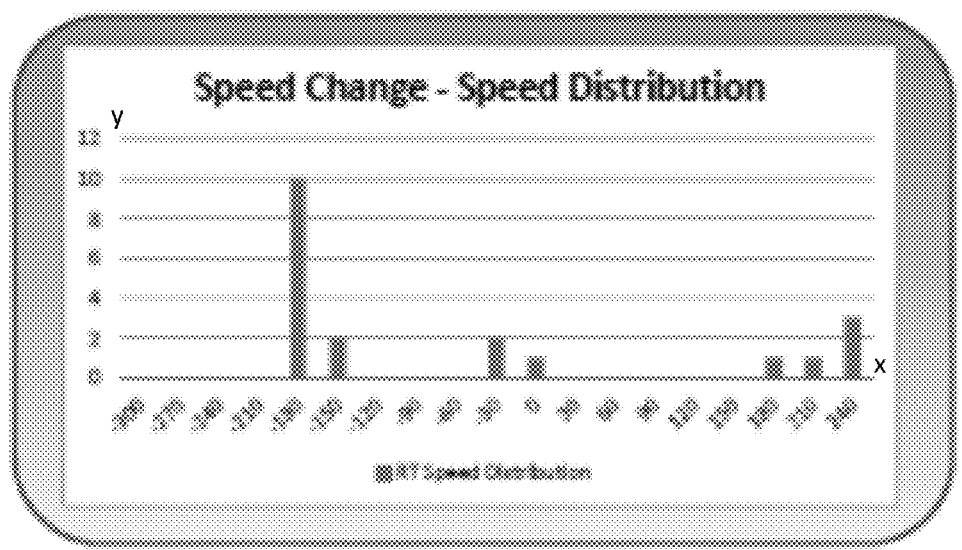
FIGS. 8A, 8B, 8C, and 8D show histogram graphs of results of the speed change, speed distribution of a right shoulder for a healthy, injured, feigned injury, and an exaggerated injury, respectively.
Figure 8B:
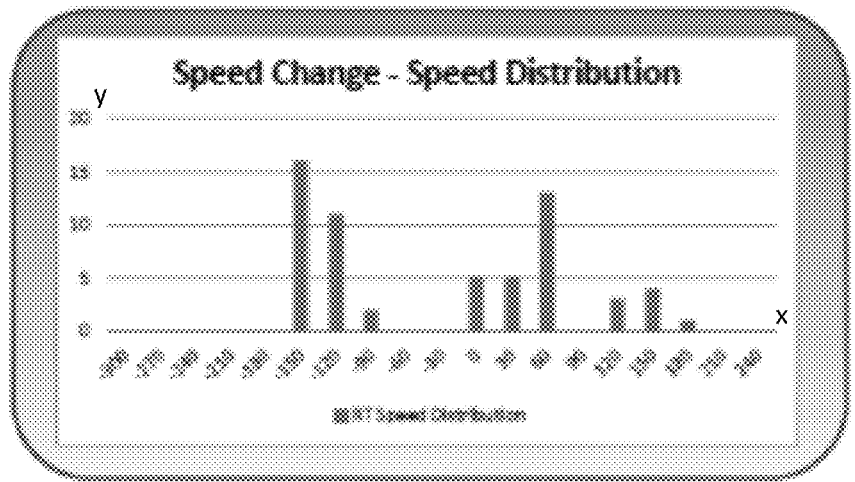
Figure 8C:
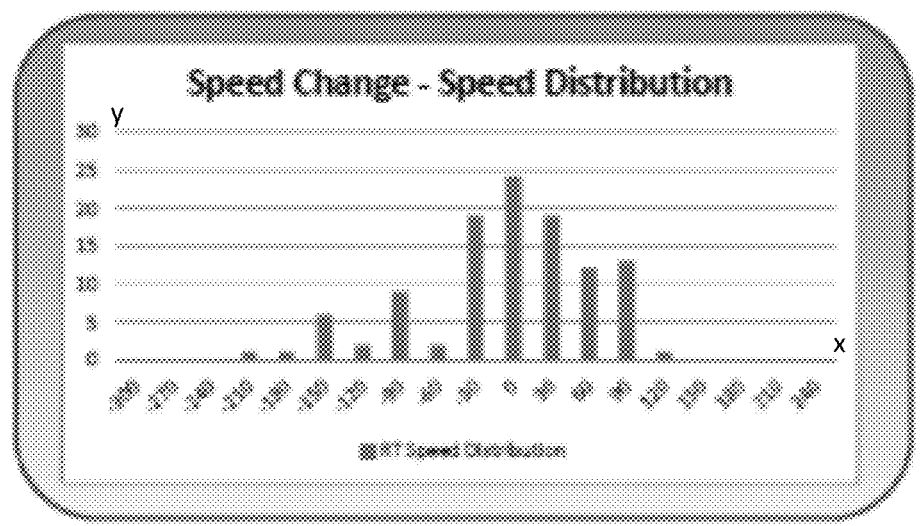
Figure 8D:
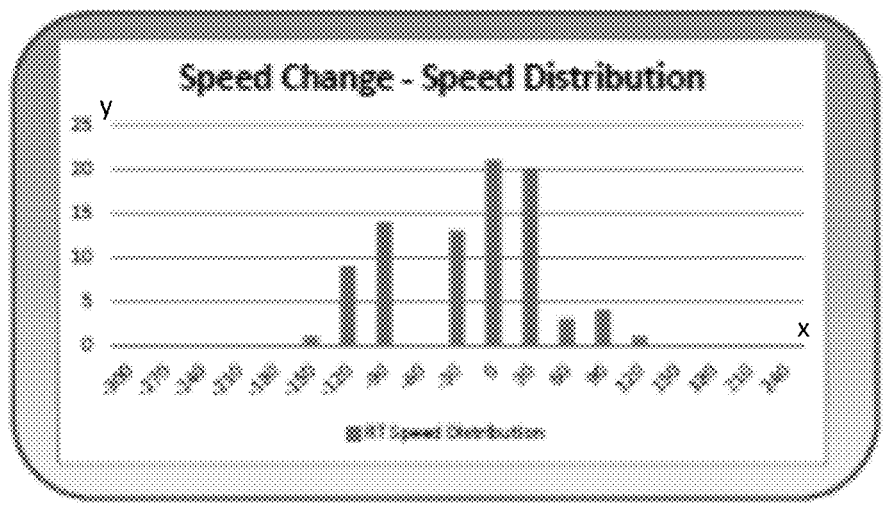
Figure 9A:
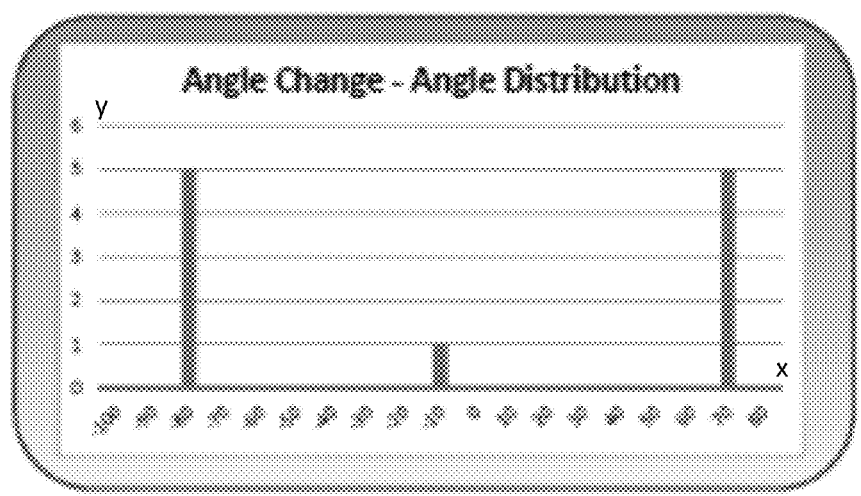
FIGS. 9A, 9B, 9C, and 9D show histogram graphs of the results of the angle change, angle distribution of a right shoulder for a healthy, injured, feigned injury, and an exaggerated injury, respectively.
Figure 9B:
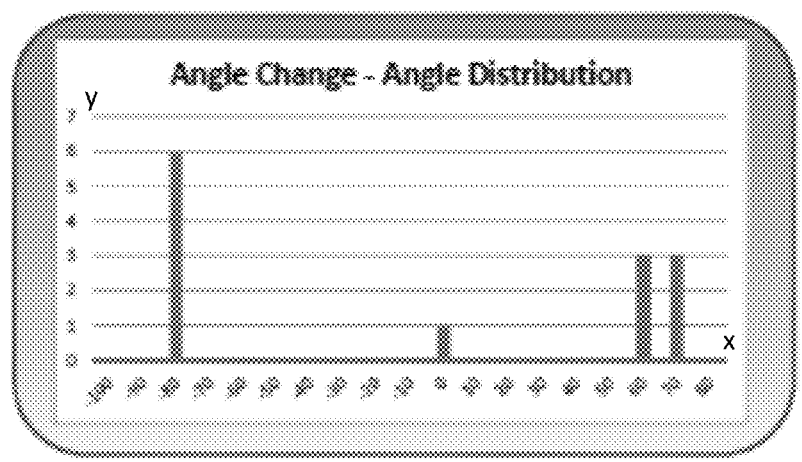
Figure 9C:
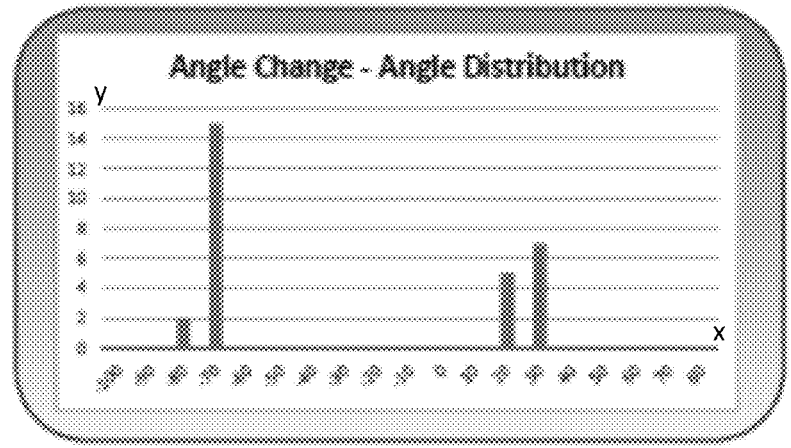
Figure 9D:
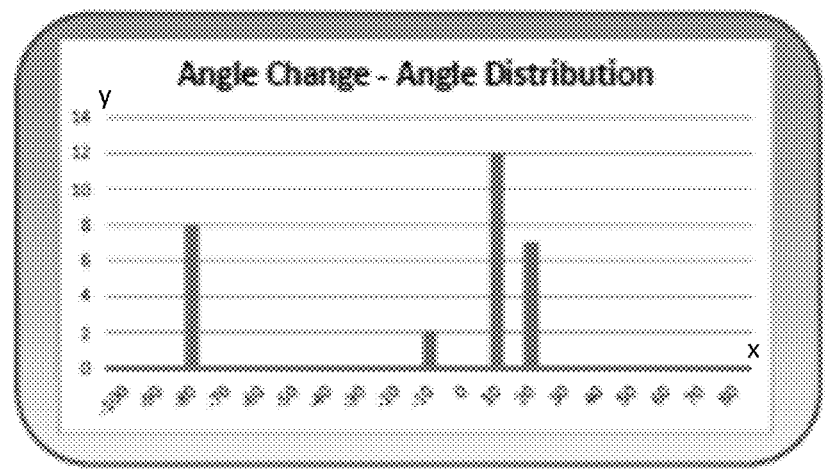
Figure 10A:
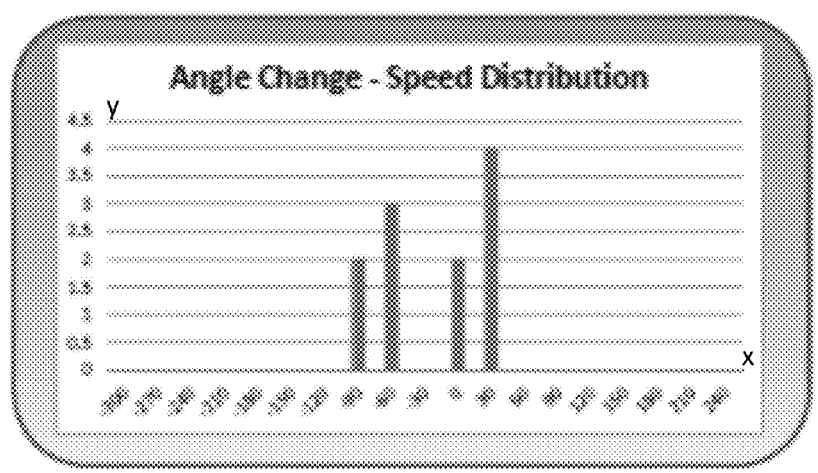
FIGS. 10A, 10B, 10C, and 10D show histogram graphs of the results of the angle change, speed distribution of a right shoulder for a healthy, injured, feigned injury, and an exaggerated injury, respectively.
Figure 10B:
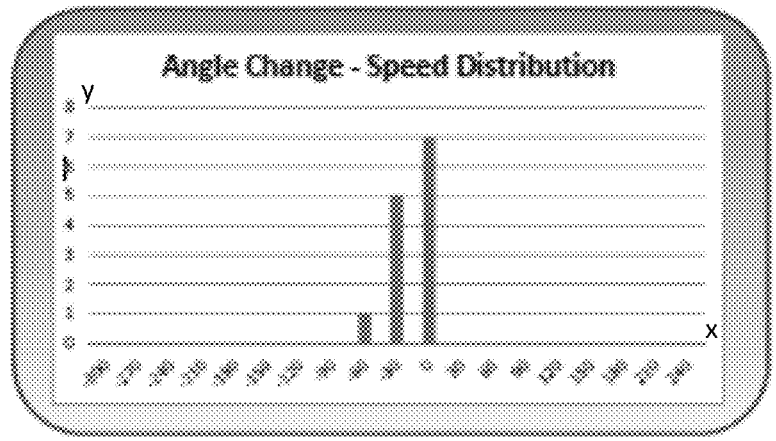
Figure 10C:
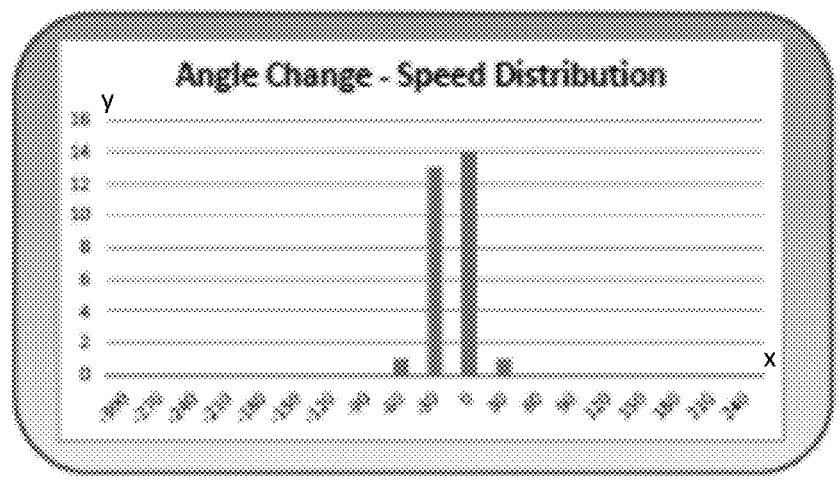
Figure 10D:
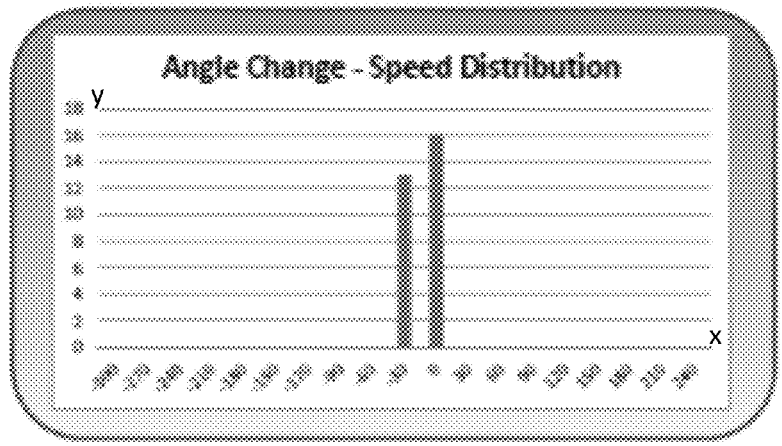

In general, a healthy joint shows a very consistent pattern of movement (i.e., consistent angular speed between rotational positions,) as shown in FIG. 4A, and an injured joint shows consistent inflection points at the point of injury (i.e., at the same rotational position,) as shown in FIG. 4B. On the other hand, feigned or exaggerated injuries show very little consistency during movement, as shown in FIGS. 4C and 4D, respectively. With reference to the healthy shoulder of FIG. 4A, the inflection points exhibit a more compact pattern as compared to the patterns of inflection points of FIGS. 4B, 4C, and 4D. The graph of FIG. 4B showing the inflection points of an injured shoulder are more spaced apart, however, still further, the inflection points of the feigned injury of FIG. 4C are less repeated and even more spaced apart than that of FIG. 4B and FIG. 4D showing the exaggerated injury.

A computing device, such as computing device 110, or an operator may compare the patient's inflection points to those of the other users to determine whether a patient is feigning an injury, exaggerating an injury, and/or is actually injured. For instance, a patient's data may be captured using sensors and a report generated, which shows the inflection points of the patient's right shoulder movement such as in FIGS. 4A-4D. For example, the report may show the number of inflection points, location of the inflection points, and how consistently positioned the inflection points are may be made against the reference information for at least one of the following: a healthy shoulder, an injured shoulder, and a feigned or exaggerated injury of a shoulder.

Referring to FIGS. 5A-5D, graphs are shown of the pattern of the abduction of the right shoulder over time. As shown in a comparison of the figures, the peaks and/or troughs of the feigned (FIG. 5C) and exaggerated (FIG. 5D) injury shoulders have inconsistent profiles and values as compared to the injured (FIG. 5B) and healthy (FIG. 5A) shoulders. Additionally, the graphs of FIGS. 6A-6D show the angular speed over time of the respective shoulders, each having a unique pattern.

FIGS. 7A-7D and FIGS. 8A-8D show unique histograms that represent the number of inflection points due to speed change. In particular, FIGS. 7A-7D illustrates the distribution based on the inflection counts of rotational position (i.e., the light grey, triangular markers in FIGS. 4A-4D, respectively), and FIGS. 8A-8D illustrates the distribution based on the inflection counts by angular speed (i.e., the darker grey, circular markers in FIGS. 4A-4D, respectively).

FIG. 9A-9D and FIGS. 10A-10D show histograms that represent the count of inflection points due to angle change, with FIGS. 9A-9D showing the count based on angle and FIGS. 10A-10D showing the count based on angular speed. Once again, by comparing the histograms of each of the categories (healthy, injured, feigned, and exaggerated injury), it can be seen that each category has its own unique pattern for each of the characteristics.

After the distributions of inflection points are produced, the distributions can be measured for statistical significance using the 2D Histogram Hypothesis Test. During the statistical analysis, each local minimum and local maximum is measured by comparing the slope of adjacent points. A local maximum is found when the slope is greater than the slope of the points before or after, and a minimum is found when the slope is less than the slope of the points before or after. In other words, if a slope of points before and after any point switches from a positive to a negative the point is a local minimum or from a negative to a positive, the point is a local maximum.

For determining the statistical significance of the values, a table of known healthy movements is compared to the subject's movements based on the subject's distribution of inflection points as described above. For example, the tests employed may be the Student's T Test and/or the Chi-squared Test. In such instances, the expected frequencies are calculated based on the conditions of the null hypothesis. The rejection of the null hypothesis is based on the differences of the actual and expected value. This allows the determination if a repeated movement is not consistent (i.e. not a healthy or injured body part).

In other examples, the statistical analysis may be performed by other tests such as Analysis of Variance (ANOVA) to determine the statistical significance of the subject's movements.

From the statistical analysis, one or more reports are generated that offer a statistical rating indicating which category (healthy, injured, feigned, or exaggerated) the patient falls into. The evaluation may be confirmed by a trained subject, such as a trained physician.

Although the above examples used herein mostly refer to a right shoulder, the systems and methods described above can be employed on many locations of the body, including joints such as, the wrists, knees, hips, or ankles, and other body parts including the back, cervical, and fingers. The characteristics may differ depending on the body part tested. Additionally, rather than a single joint, the systems may be used on multiple body parts including on a full body.

Additionally, although described herein in the context of determining a feigned or exaggerated injury, the disclosure shall not be limited in such scope. The systems and methods described above can be used to derive characteristics of an injured body part and repeated along the rehabilitation timeline to track the progress and development of the injury.

Motion data may be collected from a patient at a single joint, such as a shoulder, at multiple joints, or data may be collected from the full body of the patient. In this regard, the data may be collected while the body is in motion and equipped with a motion capture device. For instance, the motion data may be collected by sensors of the sensor system 90, as described above, or in any other way known in the art.

The sensors may collect data representative of the position of the joint being measured during a repeated pattern of movement. Alternatively, or in addition to, the sensors may collect images that can be used to determine certain characteristics used during statistical analysis. For instance, the sensor system 90 may capture images of the sensors and transmit such data to the computing device, such as computing device 110 of system 80. Using visual motion algorithms, the computing device 110 may track the motion of the sensors from frame to frame to determine the position and orientation of the joint being measured. Based upon the change in position and orientation, the velocity and/or acceleration of the joint being measured may be determined. Although collection of a patient's single joint is described, the motion data may correspond to the movement of multiple joints. For instance, the motion data may correspond to the movement of a wrist in conjunction with an elbow.

All or a portion of the data may be analyzed using instructions, such as instructions 116, to determine one or more characteristics related to the patient's motion. The characteristics may be those described in FIGS. 3-10 above. For example, FIGS. 3-10 show characteristics based on the movement of a patient's shoulder. Such characteristics may include, as shown in FIGS. 3-10, angular speed, inflection points, abduction (ABD), and angular speed. The counts of the inflection points can produce speed change and angle change distributions that are each based on the inflection counts of angle and angular speed. The characteristics listed above and described in further detail below, are not intended to limit the scope of the disclosure to such characteristics, rather, it is intended that any characteristic related to the motion of a joint of the body be considered at this step.

The distributions are then statistically analyzed to determine a statistical rating of the relative severity of the injury. For example, a rating of 10 may be extremely impaired and a rating of 1 may be healthy.

Subsequently, the patient can be tested a second time, after a certain amount of time has passed, to produce a second statistical rating of the measurement of the severity of injury to determine the progression and healing of the injury. The method may be repeated a plurality of times along the rehabilitation timeline to track the progress and development of the injury.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of tracking patient rehabilitation comprising:
   transmitting a first coordinate data set from a first image data indicative of position of one or more sensors on a body part of a patient as the body part repeatedly performs a movement at a first time to a computing device with one or more processors, the first coordinate data set being obtained by tracking the position of the one or more sensors from the first image data using a visual motion algorithm;
   transmitting a second coordinate data set from a second image data indicative of position of the one or more sensors on the body of the patient as the body part repeatedly performs the movement at a second time to the computing device, the movement performed by the body part at the second time being the same as the movement performed by the body part at the first time, the second coordinate data set being obtained by tracking the position of the one or more sensors from the second image data using the visual motion algorithm;
   determining a first set of inflection points from the first coordinate data set using the computing device, each inflection point of the first set of inflection points corresponding to a local maximum or minimum value of the first coordinate data set;
   determining a first cluster of observations from the first set of inflection points to identify a first pattern;
   determining a second set of inflection points from the second coordinate data set using the computing device, each inflection point of the second set of inflection points corresponding to a local maximum or minimum value of the second coordinate data set;
   determining a second cluster of observations from the second set of inflection points to identify a second pattern;
   comparing the first pattern to the second pattern via a statistical analysis by the computing device to determine a difference between the first pattern and the second pattern; and identifying a condition of the body part according to the difference,
wherein determining the difference includes determining a statistical difference via the statistical analysis using a chi-squared test, Analysis of Variance Test (ANOVA), and/or 2D Histogram Hypothesis Test.

2. The method of claim 1, wherein the first and second coordinate data sets include Cartesian coordinates.

3. The method of claim 1, wherein identifying the condition of the body part includes tracking rehabilitation progress from an injury to the body part.

4. The method of claim 1, wherein identifying the condition of the body part includes tracking development of an injury to the patient.

5. The method of claim 1, wherein the second time is later than the first time.

6. The method of claim 1, wherein the body part is a plurality of body parts of the patient.

7. The method of claim 1, wherein the body part is any of a shoulder, hip, and leg.

8. A system comprising:
a sensor system configured to collect position coordinate data indicative of position of one or more sensors on a moving body part through a range of motion, the sensor system configured to transmit the position coordinate data to a computing device with one or more processors, the position coordinate data being obtained by tracking the position of the one or more sensors from an image data using a visual motion algorithm;
the one or more processors configured to:
determine a first set of inflection points from a first position coordinate data set indicative of position the moving body part through the range of motion at first time and a second set of inflection points from a second position coordinate data set of the moving body part through the range of motion at a second time, the range of motion at the first time being the same as the range of motion at the second time, at least one inflection point of the first set of inflection points corresponding to a local maximum or minimum value of the first coordinate data set, at least one inflection point of the second set of inflection points corresponding to a local maximum or minimum value of the first coordinate data set;
determine a first cluster of observations from the first set of inflection points to identify a first pattern;
determine a second cluster of observations from the second set of inflection points to identify a second pattern;
compare the first pattern to the second pattern via a statistical analysis by the computing device to determine a difference between the first pattern and the second pattern; and
identify a condition of an injury for the moving body part according to the difference,
wherein determining the difference includes determining a statistical difference via the statistical analysis using a chi-squared test, Analysis of Variance Test (ANOVA), and/or 2D Histogram Hypothesis Test.

9. The system of claim 8, wherein the condition of the injury includes injury rehabilitation or injury development.

10. The system of claim 8, wherein the second time is later than the first time.

11. The system of claim 8, wherein the body part is a plurality of body parts of the patient.

12. The system of claim 8, wherein the body part is any of a shoulder, hip, and leg.

13. A non-transitory, tangible computer-readable storage medium on which computer readable instructions of a program are stored, the instructions, when executed by one or more computing devices, cause the one or more computing devices to perform a method, the method comprising:
receiving a first coordinate data set from a first image data indicative of position of one or more sensors on a body part of a subject as the body part repeatedly performs a movement at a first time, the first coordinate data set being transmitted from the one or more sensors to the computing device, the first coordinate data set being obtained by tracking the position of the one or more sensors from the image data using a visual motion algorithm;
determining a first set of inflection points from the first coordinate data set using the computing device, at least one inflection point of the first set of inflection points corresponding to a local maximum or minimum value of the first coordinate data set;
determining a first cluster of observations from the first set of inflection points to identify a first pattern;
receiving a second coordinate data set from a second image data indicative of position of the one or more sensors on the body part of a subject as the body part repeatedly performs the movement at a second time, the movement performed by the body part at the second time being the same as the movement performed by the body part at the first time, the second coordinate data set being transmitted from the one or more sensors to the computing device, the second coordinate data set being obtained by tracking the position of the one or more sensors from the second image data using the visual motion algorithm;
determining a second set of inflection points from the second coordinate data set using the computing device, at least one inflection point of the second set of inflection points corresponding to a local maximum or minimum value of the second coordinate data set;
determining a second cluster of observations from the second set of inflection points to identify a second pattern;
comparing the first pattern to the second pattern via a statistical analysis by the computing device to determine a difference therebetween; and
identifying condition of the body part according to the difference,
wherein determining the difference includes determining a statistical difference via the statistical analysis using a chi-squared test, Analysis of Variance Test (ANOVA), and/or 2D Histogram Hypothesis Test.

14. The method of claim 13, wherein the first and second set of inflection points are related to a motion characteristic, the motion characteristic including any of angular speed or angular position, wherein determining the first set of inflection points includes representing the angular speed over time on a first axis, and representing the angular position over time on a second axis.

15. The method of claim 13, wherein identifying a condition of the body part includes a tracking a progress of a patient's injury rehabilitation.

16. The method of claim 13, wherein identifying a condition of the body part includes tracking a development of a patient's injury.

17. The method of claim 13, wherein the body part is a plurality of body parts of the patient.

* * * * *